US012569223B2

(12) United States Patent     (10) Patent No.:   US 12,569,223 B2

McLaughlin     (45) Date of Patent:    Mar. 10, 2026

(54) DISTRIBUTED PORTABLE ULTRASOUND SYSTEM

(71) Applicant: Shenzhen Mindray Bio-Medical Electronics Co., Ltd., Shenzhen (CN)

(72) Inventor: Glen W. McLaughlin, San Carlos, CA (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 544 days.

(21) Appl. No.: 17/674,484

(22) Filed: Feb. 17, 2022

(65) Prior Publication Data

US 2022/0233166 A1     Jul. 28, 2022

Related U.S. Application Data

(63) Continuation-in-part of application No. 16/240,425, filed on Jan. 4, 2019, now abandoned.

(51) Int. Cl.
    *A61B 8/00*     (2006.01)

(52) U.S. Cl.
    CPC .......... *A61B 8/4427* (2013.01); *A61B 8/4433* (2013.01); *A61B 8/546* (2013.01);
           (Continued)

(58) Field of Classification Search
    CPC ....... A61B 8/4427; A61B 8/4433; A61B 8/56; A61B 2560/0431; A61B 2560/0456; A61B 2560/0462
See application file for complete search history.

(56) References Cited

U.S. PATENT DOCUMENTS

2004/0179332 A1* 9/2004 Smith .................... A61B 50/13
                                         361/679.41
2010/0250789 A1    9/2010   Collopy
                      (Continued)

FOREIGN PATENT DOCUMENTS

CN        102309338 A     1/2012
JP         2002177266 A     6/2002

*Primary Examiner* — Keith M Raymond
*Assistant Examiner* — Andrew W Begeman
(74) *Attorney, Agent, or Firm* — Syncoda LLC; Feng Ma

(57) ABSTRACT

A distributed ultrasound system includes a portable ultrasound system comprising: one or more transmitters configured to transmit ultrasound waves into a subject region; one or more receivers configured to receive ultrasound waves from the subject region in response to the ultrasound waves transmitted into the subject region; and a portable ultrasound processing unit configured to perform ultrasound image processing for generating one or more ultrasound images of the subject region using, at least in part, the ultrasound waves received from the subject region by the one or more receivers, wherein the portable ultrasound system is hand-held and capable of being moved over a patient's body to an area proximate to the subject region; and an external ultrasound docking unit configured to receive and electrically couple with the portable ultrasound system and offload at least a portion of the ultrasound image processing from the portable ultrasound system when the portable ultrasound system is coupled to the external ultrasound docking unit, wherein the portable ultrasound system determines whether to offload the at least a portion of the ultrasound image processing based at least one of a temperature or a battery level of portable ultrasound system.

19 Claims, 7 Drawing Sheets

(52) U.S. Cl.
CPC ................ *A61B 8/56* (2013.01); *A61B 8/565* (2013.01); *A61B 2560/0431* (2013.01); *A61B 2560/0456* (2013.01); *A61B 2560/0462* (2013.01)

(56) References Cited

U.S. PATENT DOCUMENTS

| | | | | |
|---|---|---|---|---|
| 2011/0320520 | A1* | 12/2011 | Jain | G06F 9/5072 |
| | | | | 709/224 |
| 2012/0190986 | A1 | 7/2012 | Sato | |
| 2013/0116563 | A1* | 5/2013 | Ogasawara | A61B 8/464 |
| | | | | 600/440 |
| 2013/0345566 | A1* | 12/2013 | Weitzel | A61B 8/4427 |
| | | | | 600/443 |
| 2014/0024939 | A1 | 1/2014 | Kato et al. | |
| 2014/0114190 | A1* | 4/2014 | Chiang | A61B 8/4405 |
| | | | | 600/440 |
| 2014/0371592 | A1* | 12/2014 | Yamamoto | A61B 8/461 |
| | | | | 600/443 |
| 2015/0011160 | A1* | 1/2015 | Jurgovan | H04W 76/14 |
| | | | | 455/41.1 |
| 2018/0039519 | A1* | 2/2018 | Kumar | G06F 9/4812 |
| 2018/0183855 | A1 | 6/2018 | Sabella | |
| 2020/0117513 | A1* | 4/2020 | Li | G06F 9/5005 |
| 2020/0205769 | A1* | 7/2020 | Kotian | A61B 6/542 |

* cited by examiner

Figure 2:
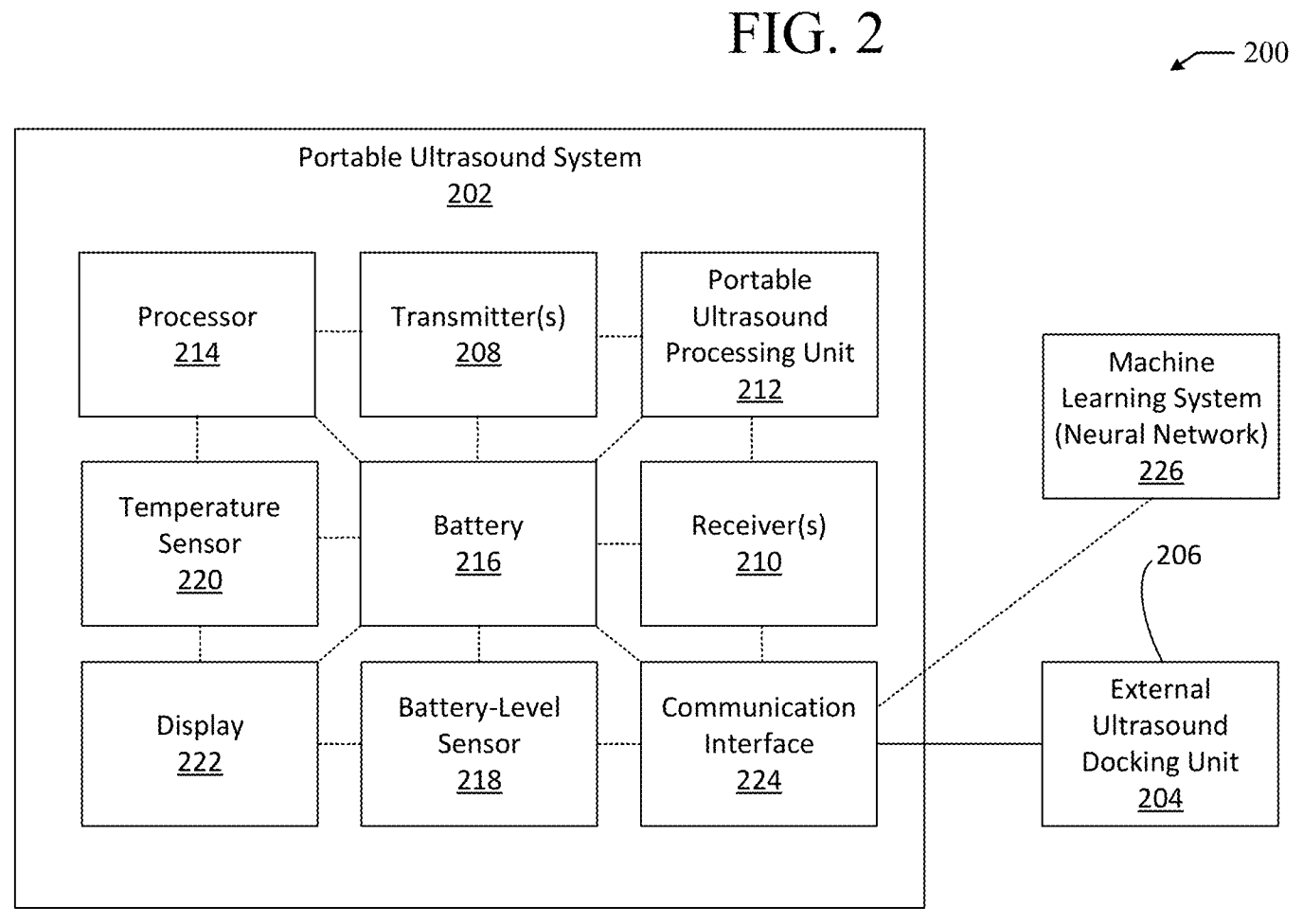

Machine Learning System (Neural Network) 226

206

External Ultrasound Docking Unit 204

Portable Ultrasound System 202

Portable Ultrasound Processing Unit 212

Receiver(s) 210

Communication Interface 224

Transmitter(s) 208

Battery 216

Battery-Level Sensor 218

Processor 214

Temperature Sensor 220

Display 222

Figure 6:
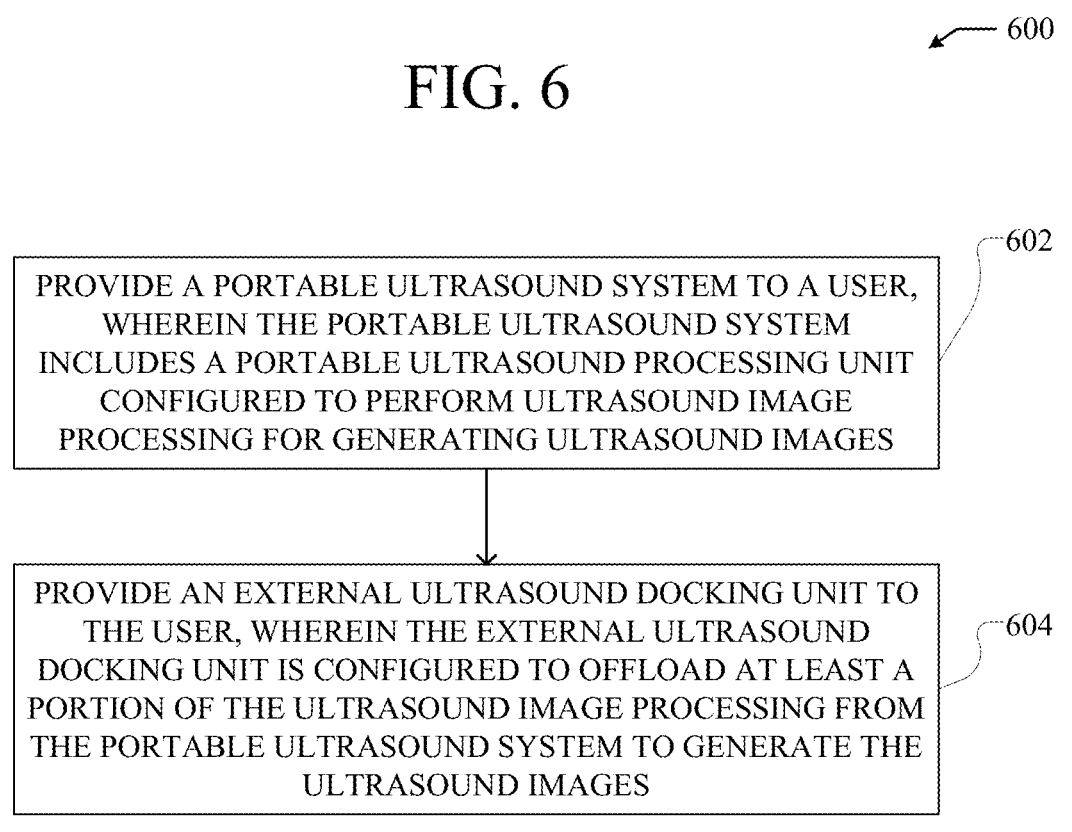

PROVIDE A PORTABLE ULTRASOUND SYSTEM TO A USER, WHEREIN THE PORTABLE ULTRASOUND SYSTEM INCLUDES A PORTABLE ULTRASOUND PROCESSING UNIT CONFIGURED TO PERFORM ULTRASOUND IMAGE PROCESSING FOR GENERATING ULTRASOUND IMAGES

604

PROVIDE AN EXTERNAL ULTRASOUND DOCKING UNIT TO THE USER, WHEREIN THE EXTERNAL ULTRASOUND DOCKING UNIT IS CONFIGURED TO OFFLOAD AT LEAST A PORTION OF THE ULTRASOUND IMAGE PROCESSING FROM THE PORTABLE ULTRASOUND SYSTEM TO GENERATE THE ULTRASOUND IMAGES

Figure 7:
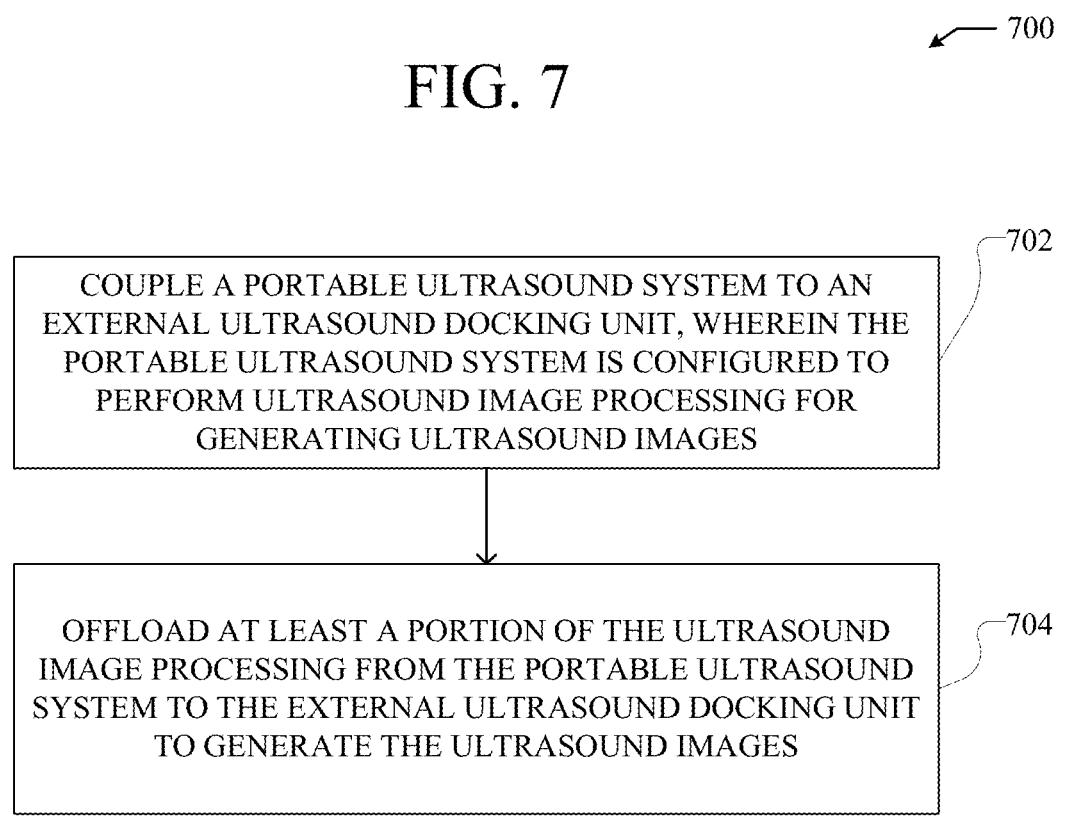

```
COUPLE A PORTABLE ULTRASOUND SYSTEM TO AN
EXTERNAL ULTRASOUND DOCKING UNIT, WHEREIN THE
PORTABLE ULTRASOUND SYSTEM IS CONFIGURED TO
PERFORM ULTRASOUND IMAGE PROCESSING FOR
GENERATING ULTRASOUND IMAGES
```
702

```
OFFLOAD AT LEAST A PORTION OF THE ULTRASOUND
IMAGE PROCESSING FROM THE PORTABLE ULTRASOUND
SYSTEM TO THE EXTERNAL ULTRASOUND DOCKING UNIT
TO GENERATE THE ULTRASOUND IMAGES
```
704

DISTRIBUTED PORTABLE ULTRASOUND SYSTEM

CROSS-REFERENCE TO RELATED APPLICATIONS

This application is a continuation-in-part of U.S. patent application Ser. No. 16/240,425, filed Jan. 4, 2019, for DISTRIBUTED PORTABLE ULTRASOUND SYSTEM, which is incorporated herein by reference.

TECHNICAL FIELD

This disclosure relates to distributed ultrasound imaging systems. Specifically, this disclosure relates to distributing processing between a portable system of a distributed ultrasound imaging system and an external ultrasound docking unit of the distributed ultrasound imaging system, e.g. for providing high-performance ultrasound image processing.

BACKGROUND OF THE INVENTION

Ultrasound systems have continued to advance in channel count, image processing and portability. The requirement for greater portability has been at odds with systems with high channel count and high-performance image processing capabilities, e.g. 3D TEE, 3D TTE, and other high computational demand processes. Specifically, the increased computational resources needed for functioning according to high-performance image processing capabilities can make portable ultrasounds incapable for portable operation. More specifically, providing high-performance image processing capabilities can increase needed computational resources and power for performing such high-performance processes in a real time manner at a high level of quality. In turn, these increased demands for computational resources and computational power can further burden the size, weight, battery life, cooling, and the like of components in a portable ultrasound system. There therefore, exist needs for portable ultrasound systems and processing methods that allow for high-performance ultrasound processing in a portable ultrasound system.

Further, typical ultrasound systems contain a substantial amount of proprietary hardware. The performance of this proprietary hardware is what typically differentiates the performance characteristics of these systems. Over the years, the amount of proprietary hardware contained within ultrasound systems has steadily decreased, however some current systems still include proprietary hardware. Proprietary hardware in ultrasound systems can limit the incorporation of industry advances in both hardware and processing methods, e.g. made in the ultrasound industry and other industries, into such ultrasound systems. For example, advances in parallel processing components made in the gaming industry are not easily adaptable for ultrasound systems as typical ultrasound systems utilize proprietary hardware. There therefore, exist needs for portable ultrasound systems and processing methods that are compatible with advances in hardware and processing methods, e.g. from both the ultrasound industry and other industries, in order to achieve high-performance ultrasound processing in a portable ultrasound system.

SUMMARY

In various embodiments, a distributed ultrasound system includes a portable ultrasound system and an external ultrasound docking unit. The portable ultrasound system can include one or more transmitters configured to transmit ultrasound waves into a subject region. Further, the portable ultrasound system can include one or more receivers configured to receive ultrasound waves from the subject region in response to the ultrasound waves transmitted into the subject region. Additionally, the portable ultrasound system can include a portable ultrasound processing unit configured to perform ultrasound image processing for generating one or more ultrasound images of the subject region using the ultrasound waves received by the one or more receivers. The external ultrasound docking unit is configured to receive the portable ultrasound system and offload at least a portion of the ultrasound image processing from the portable ultrasound system when the portable ultrasound system is coupled to the external ultrasound docking unit.

In certain embodiments, a portable ultrasound system is provided to a user. The portable ultrasound system can include one or more transmitters configured to transmit ultrasound waves into a subject region. Further, the portable ultrasound system can include one or more receivers configured to receive ultrasound waves from the subject region in response to the ultrasound waves transmitted into the subject region. Additionally, the portable ultrasound system can include a portable ultrasound processing unit configured to perform ultrasound image processing for generating one or more ultrasound images of the subject region using the ultrasound waves received by the one or more receivers. Additionally, an external ultrasound docking unit is provided. The external ultrasound docking unit can be configured to receive the portable ultrasound system and offload at least a portion of the ultrasound image processing from the portable ultrasound system when the portable ultrasound system is coupled to the external ultrasound docking unit.

In various embodiments, a portable ultrasound system is coupled to an external ultrasound docking unit. The portable ultrasound system can be configured to receive ultrasound waves from a subject region in response to ultrasound waves transmitted into the subject region. The portable ultrasound system can also be configured to generate one or more ultrasound images of the subject region through ultrasound image processing using the ultrasound waves received from the subject region. Further, at least a portion of the ultrasound image processing can be offloaded from the portable ultrasound system to the external ultrasound docking unit to generate the one or more ultrasound images. Specifically, the at least the portion of the ultrasound image processing can be offloaded to the external ultrasound docking unit through the coupling of the portable ultrasound system to the external ultrasound docking unit in order to generate the one or more ultrasound images.

BRIEF DESCRIPTION OF THE DRAWINGS

FIG. 2 shows an example distributed ultrasound system.

FIG. 3 shows a block diagram of a distributed ultrasound system with an expansion communication bus for enhanced image processing capabilities.

FIG. 6 is a flowchart of an example method of providing a distributed ultrasound system configured to offload processing from a portable ultrasound system in the distributed ultrasound system.

FIG. 7 is a flowchart of an example method of offloading processing from a portable ultrasound system in a distributed ultrasound system.

DETAILED DESCRIPTION

Figure 1:
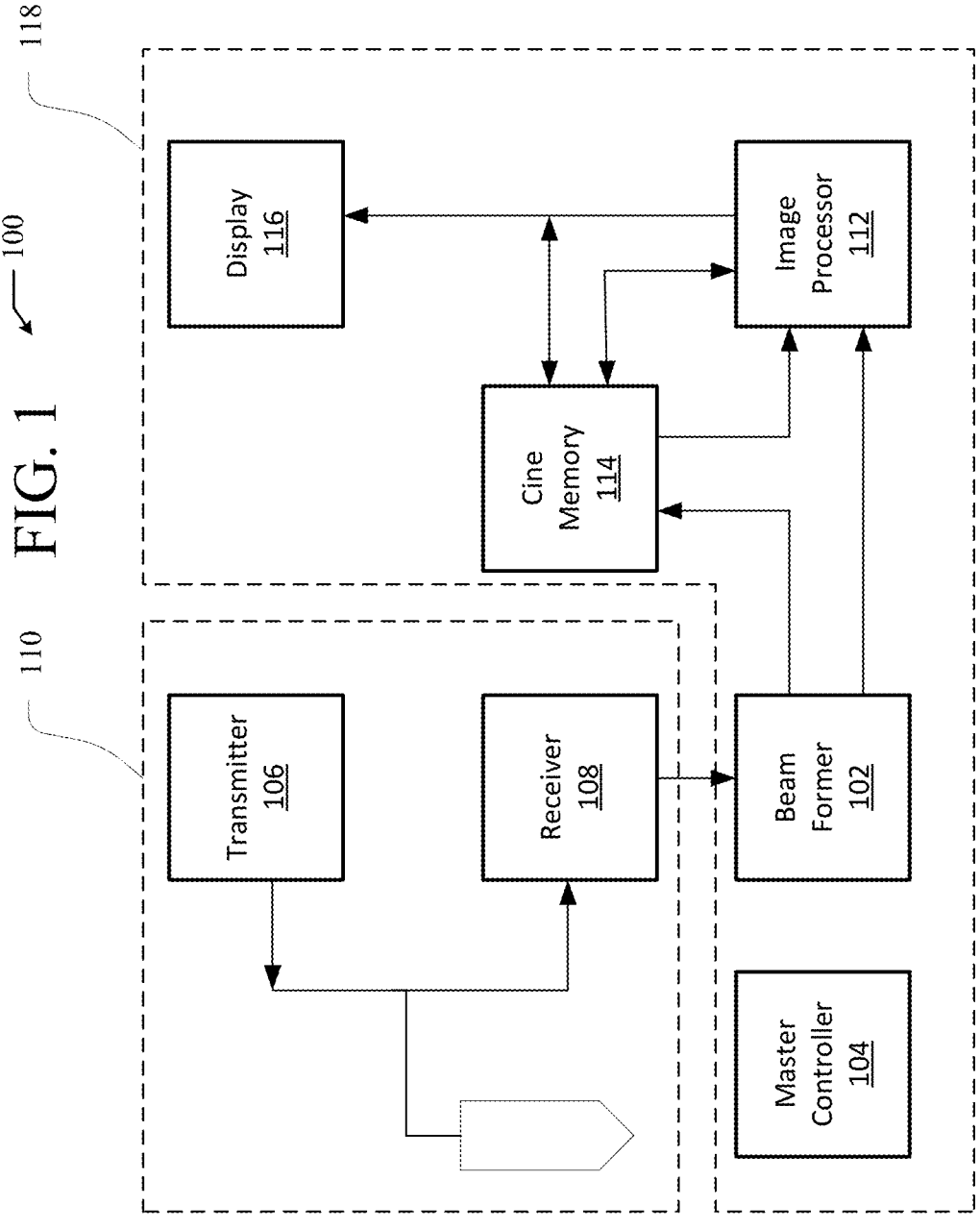
FIG. 1 illustrates an example of an ultrasound system.

The disclosure relates to the need in the art for portable ultrasound systems that can be used to provide high-performance ultrasound image processing. Specifically, the disclosure relates to systems, methods, and computer-readable media for distributing ultrasound image processing between a portable ultrasound system and an external ultrasound docking unit to provide high-performance ultrasound image processing.

Ultrasound systems have continued to advance in channel count, image processing and portability. As ultrasound systems have continued to advance, the desire for greater portability has been at odds with systems with high channel count and high-performance image processing capabilities. Specifically, when a portable ultrasound system is operated in hand, e.g. separate from an ultrasound cart/docking unit, basic ultrasound image processing operations can be performed. For example, 2D, Color Doppler, PW-Doppler, CEUS, M-Mode, CW-Doppler, biplane exams and the like low-performance image processing exams can be performed when a portable ultrasound system is operated separate from or otherwise detached from a cart. Conversely, when a portable ultrasound system is docked in a cart/docking unit, high performance ultrasound image processing operations can be performed. For example, exams like 3D TEE, 3D TTE and the like high-performance ultrasound image processing exams can be performed when a portable ultrasound system is docked in a cart.

Such high-performance ultrasound image processing exams can require a substantial amount of additional processing power to perform in a real time manner at a high level of quality. Specifically, these high-performance ultrasound image processing exams require a greater amount of processing power to perform than an amount of processing power needed to perform low-performance imaging processing operations/exams. This additional image processing power, if included in the hand carried portable ultrasound system, can provide additional burdens on one or a combination of the size, weight, battery life, cooling and the like, making a portable ultrasound system capable of performing high-performance ultrasound image processing unpractical. However, this extra processing power is not required when the portable ultrasound system is operated in hand, but only when the system is docked in the cart. Therefore, a distributed processing system is needed that has the capabilities to enhance the image processing capabilities of a portable ultrasound system when it is docked in a cart. Further, there exist needs for a distributed processing system that does not hinder operation of a portable ultrasound system when it is operated in hand, e.g. undocked from a cart.

Additionally, ultrasound systems have been constructed with a substantial amount of proprietary hardware. Specifically, the overall performance of the hardware implemented in ultrasound systems can differentiate the performance characteristics of those systems. Over the years the amount of proprietary hardware contained within a system has steadily decreased and currently a number of systems contain no proprietary hardware at all. These systems differentiate themselves on their basic architecture, algorithms and processing power. Typically, newer designed systems have the ability to take advantage in processing power from other industries like; gaming, scientific computing, virtual reality/augmented reality and the like, so that they contain substantially more processing power than the early systems. Further, as these ultrasound systems can borrow technological advances from other industries, their basic electronics outside the increased processing power change only very little.

Further, the custom architecture in ultrasound systems can also be dictated by the required signal bandwidth being higher than industry standard bus architectures. Over the years this gap has also closed to the point that current industry standard bus architectures have sufficient bandwidth to alleviate the need for custom architectures. This is also another step that has enabled the simplification of the basic ultrasound architecture and enabled industry standards to be used for communications between most if not all of the modules within ultrasound systems.

A number of the processing advancements have been achieved with using more parallel processors and the incorporation of optimized arithmetic blocks in programmable logic. Specifically, parallel processors have been exploited in Graphical Processing Units (GPUs), Digital Signal Processors (DSPs), Central Processing Units (CPUs), while the optimized arithmetic blocks have been incorporated in Field Programmable Gate Arrays (FPGAs). The exploitation of being able to replicate existing designs in parallel with minimum changes along with an on-chip optimized communication bus can enable such ultrasound systems to improve in performance in at a steady pace. In particular these systems can improve at a steady pace while the chips that have relied on continually higher clock frequencies have reached a plateau and the chip performance improves are at a much slower pace. Unfortunately, as these devices continue to drive to higher and higher performance, the system requirements in power and cooling continue to be significant. Specifically, the industry has optimized for maximizing performance and pushed the design limits to the maximum power and heat dissipation possible to achieve performance goals. These high levels of power and heat pose an issue when these devices are desired to be used in a portable ultrasound system that is battery operated. Specifically, in order to meet power and heat dissipation requirements, the industry has had to utilize older generation devices that operate at a substantially lower level of performance but also consume less power and require less cooling.

Given that portable ultrasound systems are rarely taken from the carts they are docked into, there is the potential to still maintain a portable ultrasound system capable of integration with a system for performing high-performance ultrasound image processing away from the cart. Specifically, the portable ultrasound systems can be configured to provide high-performance ultrasound image processing when integrated with the carts, as the carts provide improved storage capacity, the ability to connect multiple transducers, print capabilities, expanded connectivity, along with potentially additional battery capacity for being able to power the system without the need to plug into the electrical outlet. Specifically, the overall processing performance of distributed ultrasound systems including portable ultrasound systems can be augmented while it is docked into the cart.

More specifically, when the portable ultrasound system is docked in a cart, it is desirable that the system connect to the cart through an expansion bus, e.g. potentially automatically. This can enable the portable ultrasound system to be able to have augmented performance capabilities from both battery operation as well as processing. A typical communication bus can be, for example, a PCIe Version 5.0 with 16 lanes to have a transfer rate of over 32 GB/sec, which is more than sufficient to handle both the backend image processing requirements but also sufficient to benefit image formation capabilities as well. The benefits of using an industry standard bus architecture is that an off the shelf processing module can be used. There are several groups that make these modules, such as nVidia®, Texas Instruments®, Intel®, Xilinx® and the like. The challenge of these off the shelf processing cards is that they take up more space as well as consume a substantial amount of power to operate as compared to the processors that contained within portable ultrasound systems. The advantage is that these off the shelf processors offer the best performance as well as can be cost effectively exchanged as new technology becomes available without substantial additional costs for the product, design, or regulatory. It should be easily understood to anyone skilled in the art that just using a bus expansion as well as added battery capabilities is only a few of the features that can be offloaded to the cart for augmented performance. For example, other features that have performance/user experiences capable of being augmented by the cart/docking unit are as following: display, user interface, external connectivity, digital storage, and the like.

In various embodiments, a distributed ultrasound system includes a portable ultrasound system and an external ultrasound docking unit. The portable ultrasound system can include one or more transmitters configured to transmit ultrasound waves into a subject region. Further, the portable ultrasound system can include one or more receivers configured to receive ultrasound waves from the subject region in response to the ultrasound waves transmitted into the subject region. Additionally, the portable ultrasound system can include a portable ultrasound processing unit configured to perform ultrasound image processing for generating one or more ultrasound images of the subject region using the ultrasound waves received by the one or more receivers. The external ultrasound docking unit is configured to receive the portable ultrasound system and offload at least a portion of the ultrasound image processing from the portable ultrasound system when the portable ultrasound system is coupled to the external ultrasound docking unit.

In certain embodiments, a portable ultrasound system is provided to a user. The portable ultrasound system can include one or more transmitters configured to transmit ultrasound waves into a subject region. Further, the portable ultrasound system can include one or more receivers configured to receive ultrasound waves from the subject region in response to the ultrasound waves transmitted into the subject region. Additionally, the portable ultrasound system can include a portable ultrasound processing unit configured to perform ultrasound image processing for generating one or more ultrasound images of the subject region using the ultrasound waves received by the one or more receivers. Additionally, an external ultrasound docking unit is provided. The external ultrasound docking unit can be configured to receive the portable ultrasound system and offload at least a portion of the ultrasound image processing from the portable ultrasound system when the portable ultrasound system is coupled to the external ultrasound docking unit.

In various embodiments, a portable ultrasound system is coupled to an external ultrasound docking unit. The portable ultrasound system can be configured to receive ultrasound waves from a subject region in response to ultrasound waves transmitted into the subject region. The portable ultrasound system can also be configured to generate one or more ultrasound images of the subject region through ultrasound image processing using the ultrasound waves received from the subject region. Further, at least a portion of the ultrasound image processing can be offloaded from the portable ultrasound system to the external ultrasound docking unit to generate the one or more ultrasound images. Specifically, the at least the portion of the ultrasound image processing can be offloaded to the external ultrasound docking unit through the coupling of the portable ultrasound system to the external ultrasound docking unit in order to generate the one or more ultrasound images.

Some of the infrastructure that can be used with embodiments disclosed herein is already available, such as general-purpose computers, computer programming tools and techniques, digital storage media, and communications networks. A computing device may include a processor such as a microprocessor, microcontroller, logic circuitry, or the like. The processor may include a special purpose processing device such as an ASIC, PAL, PLA, PLD, FPGA, or other customized or programmable device. The computing device may also include a computer-readable storage device such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

FIG. 1 illustrates an example of an ultrasound system 100. The ultrasound system 100 shown in FIG. 1 is merely an example system and in various embodiments, the ultrasound system 100 can have less components or additional components. The ultrasound system 100 can be an ultrasound system where the receive array focusing unit is referred to as a beam former 102, and image formation can be performed on a scanline-by-scanline basis. System control can be centered in the master controller 104, which accepts operator inputs through an operator interface and in turn controls the various subsystems. For each scan line, the transmitter 106 generates a radio-frequency (RF) excitation voltage pulse waveform and applies it with appropriate timing across the transmit aperture (defined by a sub-array of active elements) to generate a focused acoustic beam along the scan line. RF echoes received by the receive aperture 108 of the transducer 110 are amplified and filtered by the receiver 108, and then fed into the beam former 102, whose function is to perform dynamic receive focusing; i.e., to re-align the RF signals that originate from the same locations along various scan lines.

The image processor 112 can perform processing specific to active imaging mode(s) including 2D scan conversion that transforms the image data from an acoustic line grid to an X-Y pixel image for display. For Spectral Doppler mode, the image processor 112 can perform wall filtering followed by spectral analysis of Doppler-shifted signal samples using typically a sliding FFT-window. The image processor 112 can also generate the stereo audio signal output corresponding to forward and reverse flow signals. In cooperation with the master controller 104, the image processor 112 also can format images from two or more active imaging modes, including display annotation, graphics overlays and replay of cine loops and recorded timeline data.

The cine buffer 114 provides resident digital image storage for single image or multiple image loop review, and acts as a buffer for transfer of images to digital archival devices. On most systems, the video images at the end of the data processing path can be stored to the cine memory. In state-of-the-art systems, amplitude-detected, beamformed data may also be stored in cine memory 114. For spectral Doppler, wall-filtered, baseband Doppler 1/Q data for a user-selected range gate can be stored in cine memory 114. Subsequently, the display 116 can display ultrasound images created by the image processor 112 and/or images using data stored in the cine memory 114.

The beam former 102, the master controller 104, the image processor, the cine memory 114, and the display can be included as part of a main processing console 118 of the ultrasound system 100. In various embodiments, the main processing console 118 can include more or fewer components or subsystems. The ultrasound transducer 110 can be incorporated in an apparatus that is separate from the main processing console 118, e.g. in a separate apparatus that is wired or wirelessly connected to the main processing console 118. This allows for easier manipulation of the ultrasound transducer 110 when performing specific ultrasound procedures on a patient. Further, the transducer 110 can be an array transducer that includes an array of transmitting and receiving elements for transmitting and receiving ultrasound waves.

FIG. 2 shows an example distributed ultrasound system 200. The distributed ultrasound system 200 shown in FIG. 2 can be configured to perform the functionalities of an applicable ultrasound system, such as the ultrasound system 100 shown in FIG. 1. Specifically, the distributed ultrasound system 200 can be configured to implement both high-performance ultrasound image processing and low-performance ultrasound image processing. For example, the distributed ultrasound system 200 can perform both PW Doppler imaging and 3D TEE imaging.

The distributed ultrasound system 200 includes a portable ultrasound system 202 and an external ultrasound docking unit 204. The portable ultrasound system 202 functions, at least in part, to generate ultrasound images according to an applicable ultrasound system, such as the ultrasound system 100 shown in FIG. 1. Specifically, the portable ultrasound system 202 can include one or more transmitter(s) 208 and one or more receiver(s) 210. In operation, the transmitter(s) 208 and the receiver(s) 210 can function to transmit ultrasound waves into a subject region and receive ultrasound waves from the subject region in response to the ultrasound waves transmitted into the subject region. Specifically, the transmitter(s) 208 and the receiver(s) 210 can function according to an applicable ultrasound transducer, such as the ultrasound transducer 110 shown in FIG. 1.

Further, the portable ultrasound system 202 includes a portable ultrasound processing unit 212. The portable ultrasound processing unit 212 functions to perform ultrasound image processing for generating one or more ultrasound images from ultrasound waves received by the receiver(s) 210. Specifically, the portable ultrasound processing unit 212 can perform ultrasound image processing on ultrasound waves received in response to ultrasound waves transmitted into a subject region by the transmitter(s) 208. The portable ultrasound processing unit 212 can perform applicable ultrasound image processing, such as the functionalities performed by the main processing console 118. Ultrasound image processing, as used herein, can include applicable operations applied to generate one or more ultrasound images. Specifically, ultrasound image processing can include operations for generating beamformed data from channel domain data and operations for processing post-beamformed/beamformed data to generate one or more ultrasound images. Specifically, ultrasound image processing performed by the portable ultrasound processing unit 212 can include basic/low-performance ultrasound image processing operations. For example, the portable ultrasound processing unit 212 can perform operations such as portable 2D, Color Doppler, PW-Doppler, CEUS, M-Mode, CW-Doppler, biplane exams, and the like low-performance image processing exams.

Additionally, the portable ultrasound processing unit 212 can apply applicable backend/post-processing techniques to ultrasound images, as part of performing ultrasound image processing. Specifically, the portable ultrasound processing unit 212 can apply backend processing to ultrasound images that are generated by the portable ultrasound processing unit 212. Backend processing, can include applicable image processing techniques for preparing ultrasound images for display. For example, the portable ultrasound processing unit 212 can perform, as part of backend processing, up sampling, down sampling, log compression, detection, spatial filtering, adaptive filtering, scan conversion, and the like, for displaying images.

The portable ultrasound system 202 may include a variety of additional components, including, without limitation, a processor 214 to control and coordinate the operations of the portable ultrasound system 202, a battery 216 to provide power to the system 202, a battery-level sensor 218 to measure a charging level of the battery 216, a temperature sensor 220 to measure the temperature of the system 202 and/or individual components thereof (e.g., processor 214, battery 216), a display 222 to display ultrasound images and other information (e.g., user interfaces, alerts), and a communication interface 224. These components will be described in greater detail below.

The portable ultrasound system 202 is portable in that it can be moved by a user during operation. Specifically, the portable ultrasound system 202 can be handheld. In turn, an operator can manipulate, e.g. move, the portable ultrasound system 202 over a patient's body to an area proximate to a subject region and perform an exam or otherwise gather data and generate ultrasound images including the subject region. Further, in being portable, the portable ultrasound system 202 can be removable secured to the external ultrasound docking unit 204. Specifically, the portable ultrasound system 202 can be physically detached from the external ultrasound docking unit 204 when it is operated in a portable manner.

The portable ultrasound system 202 can be coupled to the external ultrasound docking unit 204 through a docking connection 206. The docking connection 206 can be formed by either or both a physical connection and an electrical connection and may be provided using the communication interface 224 in some embodiments. In other embodiments, the communication interface 224 may be separate from the docking connection 206 and may be used for communicating with a network, such as the Internet. For example, the docking connection 206 can electrically couple the portable ultrasound system 202 to the external ultrasound docking unit 204 through either or both a wired or a wireless connection. In another example, the docking connection 206 can physically secure the portable ultrasound system 202 to the external ultrasound docking unit 204.

In various embodiments, the portable ultrasound system 202 can be moved separate from, e.g. be physically detached from, the external ultrasound docking unit 204 while the portable ultrasound system 202 is electrically coupled to the external ultrasound docking unit 204. For example, the portable ultrasound system 202 can be physically detached from the external ultrasound docking unit 204 while it is still electrically connected to the external ultrasound docking unit 204 through a wired connection. In turn, the docking connection 206 can be used to transmit data, e.g. beamformed ultrasound data, to the external ultrasound docking unit 204 from the portable ultrasound system 202 as the portable ultrasound system 202 is manipulated during operation.

The docking connection 206 can be formed by a communication bus. In being formed by a communication bus, the docking connection 206 can provide data input and data output between the portable ultrasound system 202 and the external ultrasound docking unit 204. For example, raw ultrasound data gathered by the portable ultrasound system 202 can be transferred to the external ultrasound docking unit 204 through a communication bus. Subsequently, and as will be discussed in greater detail later, the external ultrasound docking unit 204 can apply ultrasound image processing to the raw ultrasound data to generate ultrasound images. Further, in being formed by a communication bus, the docking connection 206 can be used to transfer power between the portable ultrasound system 202 and the external ultrasound docking unit 204.

In various embodiments, the docking connection 206 can be formed using industry standard/off-the-shelf connection hardware and coupling mechanisms. Specifically, a communication bus forming the docking connection 206 can be an industry standard communication bus. This can allow for easy integration of the distributed ultrasound system 200 with industry standard ultrasound image processing techniques. Further, this can allow for easy integration of the distributed ultrasound system 200 with industry standard computer processing hardware and techniques. For example, using a communication bus that is standard in the gaming industry can facilitate integration of gaming industry hardware and processing techniques into the distributed ultrasound system 200. This is advantageous as advances in processing hardware and techniques have been developed further in other industries separate from the ultrasound industry.

The external ultrasound docking unit 204 functions to receive the portable ultrasound system 202. In receiving the portable ultrasound system 202, the external ultrasound docking unit 204 can be physically and electrically coupled to the portable ultrasound system 202. Specifically, the portable ultrasound system 202 can be physically docked to the external ultrasound docking unit 204 by an operator, e.g. through docking connection 206. More specifically, concurrently with physically docking the portable ultrasound system 202 to the external ultrasound docking unit 204, the portable ultrasound system 202 can be automatically electrically coupled to the external ultrasound docking unit 204. For example, the portable ultrasound system 202 can be physically secured to the external ultrasound docking unit 204 through a mechanical structure that includes a communication bus that automatically electrically connects the portable ultrasound system 202 to the external ultrasound docking unit 204 when the portable ultrasound system 202 is physically secured to the external ultrasound docking unit 204. Alternatively, the portable ultrasound system 202 can be manually electrically connected to the external ultrasound docking unit. For example, the portable ultrasound system 202 can be physically connected to the external ultrasound docking unit 204 and a user can manually connect the portable ultrasound system 202 to an input/output port to electrically connect the portable ultrasound system 202 to the external ultrasound docking unit 204.

Additionally, the external ultrasound docking unit 204 functions to offload ultrasound image processing from the portable ultrasound system 202. The external ultrasound docking unit 204 can perform applicable ultrasound image processing, as part of offloading ultrasound image processing from the portable ultrasound system 202. Specifically, the external ultrasound docking unit 204 can perform the functionalities carried out by the main processing console 118. Further, ultrasound image processing performed by the external ultrasound docking unit 204 can include operations for generating beamformed data from channel domain data and operations for processing beamformed data to generate one or more ultrasound images. Specifically, ultrasound image processing performed by the external ultrasound docking unit 204 can include high-performance ultrasound image processing operations. For example, the external ultrasound docking unit 204 can perform operations such as 3D TEE, 3D TTE, and other high computational demand processes.

In offloading ultrasound image processing from the portable ultrasound system 202, the external ultrasound docking unit 204 can perform ultrasound image processing that the portable ultrasound processing unit 212 is unable to perform, e.g. lacks the computational resources and processing power to perform. Specifically, the external ultrasound docking unit 204, as will be discussed in greater detail later, can have a greater amount of processing power than the portable ultrasound processing unit 212. In turn, the external ultrasound docking unit 204 can be configured to perform operations that require a greater amount of computational resources than the computational resources available at the portable ultrasound processing unit 212. For example, the external ultrasound docking unit 204 can perform 3D ultrasound image processing if the portable ultrasound processing unit 212 lacks the processing power to perform 3D ultrasound image processing. Alternatively, the external ultrasound docking unit 204 can be configured to perform ultrasound image processing that the portable ultrasound processing unit 212 is able to perform, but is still offloaded to the external ultrasound docking unit 204.

Additionally, in offloading ultrasound image processing from the portable ultrasound system 202, the external ultrasound docking unit 204 can receive, from the portable ultrasound system 202, channel domain data gathered by the portable ultrasound system 202. Subsequently, the external ultrasound docking unit 204 can apply operations to the channel domain data to generate one or more ultrasound images. For example, the external ultrasound docking unit 204 can apply applicable beamforming operations to channel domain data to generate beamformed data as part of generating ultrasound images.

Further, in offloading ultrasound image processing from the portable ultrasound system 202, the external ultrasound docking unit 204 can receive, from the portable ultrasound system 202, beamformed data generated by the portable ultrasound processing unit 212. Subsequently, the external ultrasound docking unit 204 can apply operations to the beamformed data to ultimately generate one or more ultrasound images.

The external ultrasound docking unit 204 can apply applicable enhanced backend/post-processing techniques to ultrasound images, as part of offloading ultrasound image processing from the portable ultrasound system 202. Specifically, the external ultrasound docking unit 204 can apply backend processing to ultrasound images, e.g. those that are generated by either or both the portable ultrasound processing unit 212 and the external ultrasound docking unit 204 itself. Enhanced backend processing, can include applicable image processing techniques for preparing ultrasound images for display. For example, the external ultrasound docking unit 204 can perform, as part of backend processing, up sampling, down sampling, log compression, detection, spatial filtering, adaptive filtering, scan conversion, and the like, for displaying images.

The external ultrasound docking unit 204 can offload ultrasound image processing from the portable ultrasound system 202 when the portable ultrasound system 202 is electrically coupled to the external ultrasound docking unit 204. Specifically, the external ultrasound docking unit 204 can offload ultrasound image processing from the portable ultrasound system 202 when the portable ultrasound system 202 is both physically and electrically coupled to the external ultrasound docking unit 204. For example, the portable ultrasound system 202 can automatically offload processing to the external ultrasound docking unit 204 when the portable ultrasound system 202 is docked and electrically coupled to the external ultrasound docking unit 204. Further, the portable ultrasound system 202 can automatically offload processing to the external ultrasound docking unit 204 when the portable ultrasound system 202 is electrically coupled to the external ultrasound docking unit 204 even though the portable ultrasound processing unit 212 has the computational power to perform the processing. For example, even if the portable ultrasound processing unit 212 has the processing power to perform 2D image processing, the portable ultrasound system 202 can still offload the 2D image processing to the external ultrasound docking unit 204. For example, the portable ultrasound docking unit 204 may offload the 2D image processing to conserve battery power or reduce heat, as described in greater detail below.

In various embodiments, the external ultrasound docking unit 204 and the portable ultrasound processing unit 212 can be configured to perform ultrasound image processing in parallel to generate ultrasound images. Specifically, the external ultrasound docking unit 204 and the portable ultrasound processing unit 212 can perform ultrasound image processing in parallel to conserve computational resources at the external ultrasound docking unit 204 and the portable ultrasound processing unit 212. For example, the portable ultrasound processing unit 212 can apply an applicable beamforming technique to channel domain data gathered by the portable ultrasound system 202 in order to generate beamformed data. The external ultrasound docking unit 204 can subsequently process the beamformed data generated by the portable ultrasound processing unit 212 to generate ultrasound images. Further, the portable ultrasound processing unit 212 can continue to generate additional beamformed data as the external ultrasound docking unit 204 processes the beamformed data already generated by the portable ultrasound system 202.

As part of offloading processing from the portable ultrasound system 202 to the external ultrasound docking unit 204, the portable ultrasound processing unit 212 can actually determine whether to offload ultrasound image processing to the external ultrasound docking unit 204. Subsequently, the portable ultrasound processing unit 212 can offload the ultrasound image processing to the external ultrasound docking unit 204 if it determines to offload the processing. In offloading processing, and as discussed previously, the portable ultrasound processing unit 212 can send applicable data for offloading ultrasound image processing to the external ultrasound docking unit 204 if it is determined to offload the processing to the external ultrasound docking unit 204. For example, if the portable ultrasound processing unit 212 determines to offload beamforming and subsequent image creation to the external ultrasound docking unit 204, then the portable ultrasound processing unit 212 can send gathered channel domain data to the external ultrasound docking unit 204. In another example, if the portable ultrasound processing unit 212 determines to offload image creation from beamformed data to the external ultrasound docking unit 204, then the portable ultrasound processing unit 212 can send generated beamformed data to the external ultrasound docking unit 204. In yet another example, if the portable ultrasound processing unit 212 determined to offload backend processing to the external ultrasound docking unit 204, then the portable ultrasound processing unit 212 can send generated ultrasound images to the external ultrasound docking unit 204 for enhanced backend processing.

Alternatively, if the portable ultrasound processing unit 212 determines to not offload ultrasound image processing to the external ultrasound docking unit 204, then the portable ultrasound processing unit 212 can perform the ultrasound image processing. For example, if the portable ultrasound processing unit 212 determines to refrain from offloading the image processing, then the portable ultrasound processing unit 212 can form beamformed data to generate one or more ultrasound images. Further, if the portable ultrasound processing unit 212 determines to refrain from offloading the image processing, then the portable ultrasound processing unit 212 can perform backend processing on ultrasound images generated by the portable ultrasound processing unit 212.

The portable ultrasound processing unit 212 can determine whether to offload ultrasound image processing to the external ultrasound docking unit 204 based on characteristics of the ultrasound image processing. Characteristics of ultrasound image processing can include types of operations to perform in the ultrasound image processing, an amount of computational resources needed to perform the ultrasound image processing, and storage requirements needed to perform the ultrasound image processing. For example, if the portable ultrasound processing unit 212 determines that the ultrasound image processing incudes 3D image processing, then the portable ultrasound processing unit 212 can determine to offload the processing to the external ultrasound docking unit 204.

Further, the portable ultrasound processing unit 212 can determine whether to offload ultrasound image processing to the external ultrasound docking unit 204 based on an amount of available processing power at the portable ultrasound processing unit 212. Specifically, if the portable ultrasound processing unit 212 determines that it does not have enough processing power to provide specific ultrasound image processing, then the portable ultrasound processing unit 212 can determine to offload the processing to the external ultrasound docking unit 204. Alternatively, if the portable ultrasound processing unit 212 determines that it does have enough processing power to provide specific ultrasound image processing, then the portable ultrasound processing unit 212 can perform the processing itself instead of offloading the processing.

Additionally, the portable ultrasound processing unit 212 can determine whether to offload ultrasound image processing to the external ultrasound docking unit 204 based on whether the portable ultrasound system 202 is electrically coupled to the external ultrasound docking unit 204. Specifically, the portable ultrasound processing unit 212 can automatically offload all or a portion of ultrasound image processing to the external ultrasound docking unit 204 when the portable ultrasound system 202 is electrically coupled to the external ultrasound docking unit 204.

In some embodiments, the portable ultrasound processing unit 212 (or the processor 214 or other component of the portable ultrasound system 202) may determine whether to offload ultrasound image processing to the external ultrasound docking unit 204 based on the heat level of the portable ultrasound processing unit 212 (or the processor 214, the battery 216, and/or other components of the portable ultrasound system 202). Heat degrades battery performance and may cause wear on electrical components. Accordingly, the temperature of the portable ultrasound processing unit 212 may be obtained via one or more temperature sensors 220, such as a thermocouple, a resistance temperature detector (RTD), a thermistor, and/or semiconductor-based based temperature sensor included in an integrated circuit (IC) or the like. If the temperature exceeds a threshold or exceeds a threshold for a predetermined time period, the portable ultrasound processing unit 212 may determine to offload ultrasound image processing to the external ultrasound docking unit 204.

Alternatively, or in addition, the portable ultrasound processing unit 212 may determine whether to offload ultrasound image processing to the external ultrasound docking unit 204 based on the current or projected battery level of the portable ultrasound processing unit 212. For example, the portable ultrasound processing unit 212 may have sufficient processing power to perform a desired ultrasound operation, but the battery level sensor 218 may detect that the current battery level is insufficient to be able to complete the ultrasound operation or complete the ultrasound operation with a desired margin of error or cushion. In such a case, the portable ultrasound processing unit 212 may determine to offload ultrasound image processing to the external ultrasound docking unit 204.

In other embodiments, the portable ultrasound processing unit 212 may determine whether to offload ultrasound image processing to the external ultrasound docking unit 204 based on a selected examination type (e.g., transesophageal echocardiography) or a particular examination area (e.g., heart). If a transesophageal echocardiography examination type (or other examination type requiring a particular amount of processing power, storage, battery capacity, etc.) is selected, the portable ultrasound processing unit 212 may offload ultrasound image processing to the external ultrasound docking unit 204. By contrast, if a doppler examination of the heart is selected, the portable ultrasound processing unit 212 may decide to not offload ultrasound image processing to the external ultrasound docking unit 204 and perform the processing internally.

In some embodiments, the determination of whether to offload may be made with reference to prior user input. For example, the user may specify at a configuration stage, for example, that certain types of examinations should be offloaded (or not offloaded) or that certain battery capacities, storage capacities, thermal limits, or the like, should apply to the determination of whether to offload.

Alternatively, or in addition, the determination may be made using machine learning. For example, the portable ultrasound processing unit 212 may determine during a particular examination that an ultrasound operation cannot be completed in real-time within the portable ultrasound processing unit 212. Likewise, the portable ultrasound processing unit 212 may determine during an examination that certain ultrasound operations will exceed the battery capacity of the portable ultrasound processing unit 212 or result in heat levels that exceed a certain threshold within the portable ultrasound processing unit 212. Using a machine learning system 226 (e.g., neural network) accessible to the portable ultrasound processing unit 212, the portable ultrasound processing unit 212 may learn whether offloading will be required and automatically offload (or prompt a user of the necessity of offloading) in subsequent operations where offloading may be needed.

Any combination of two or more of the foregoing determinations may be combined in deciding whether to offload processing. Furthermore, determining whether to offload may include balancing factors of processing power, heat, battery capacity, storage requirements, and the like, with user settings and/or processing goals specified by the user.

At the time the determination is made to offload the processing, offloading may commence immediately if the portable ultrasound system 202 is docketed (e.g., electrically) connected to the external ultrasound docking unit 204. If the portable ultrasound system 202 is not currently electrically connected to the external ultrasound docking unit 204, the portable processing unit 212 may notify the user via any combination of audible, visual, or haptic means (e.g., light, sound, vibration), indicating that the user should connect the portable processing unit 212 to the external ultrasound docking unit 204 immediately, after a scan is finished, or within a particular time interval.

After ultrasound image processing is offloaded to the external ultrasound docking unit 204 and is actually performed by the external ultrasound docking unit 204, then the generated ultrasound images can be sent back to the portable ultrasound system 202. Specifically, ultrasound images generated at the external ultrasound docking unit 204 can be sent back to the portable ultrasound system 202 for display at the portable ultrasound system 202 or for further image processing. More specifically, the portable ultrasound system 202 can include a display for displaying ultrasound images, e.g. ultrasound images processed, at least in part, by the external ultrasound docking unit 204. For example, the external ultrasound docking unit 204 can perform enhanced backend processing on ultrasound images, and send the enhanced backend processed ultrasound images back to the portable ultrasound system 202 for display at the portable ultrasound system 202.

The external ultrasound docking unit 204 can be configured to transfer power to the portable ultrasound system 202. Specifically, the external ultrasound docking unit 204 can transfer power to the portable ultrasound system 202 through the docking connection 206, when the portable ultrasound system 202 is electrically coupled to the external ultrasound docking unit 204. Power transferred to the portable ultrasound system 202 by the external ultrasound docking unit 204 can be used to power the portable ultrasound system 202 during operation. For example, power transferred to the portable ultrasound system 202 by the external ultrasound docking unit 204 can be used to power the transmitter(s) 208 and the receiver(s) in transmitting and receiving ultrasound waves to and from a subject region. Further, power transferred to the portable ultrasound system 202 from the external ultrasound docking unit 204 can be used to recharge a power supply implemented as part of the portable ultrasound system 202. Specifically, power transferred from the external ultrasound docking unit 204 to the portable ultrasound system 202 can recharge a battery integrated as part of the portable ultrasound system 202.

The external ultrasound docking unit 204 can be implemented as part of an ultrasound cart. In being implemented in an ultrasound cart, the external ultrasound docking unit 204 can be movable as part of the cart. This is advantageous as the external ultrasound docking unit 204 can be moved to different examination rooms for performing different examinations. Further, the docking connection 206 can be implemented, at least in part, in an ultrasound cart. For example, the docking connection 206 can be formed by a communication bus implemented in an ultrasound cart.

Figure 3:
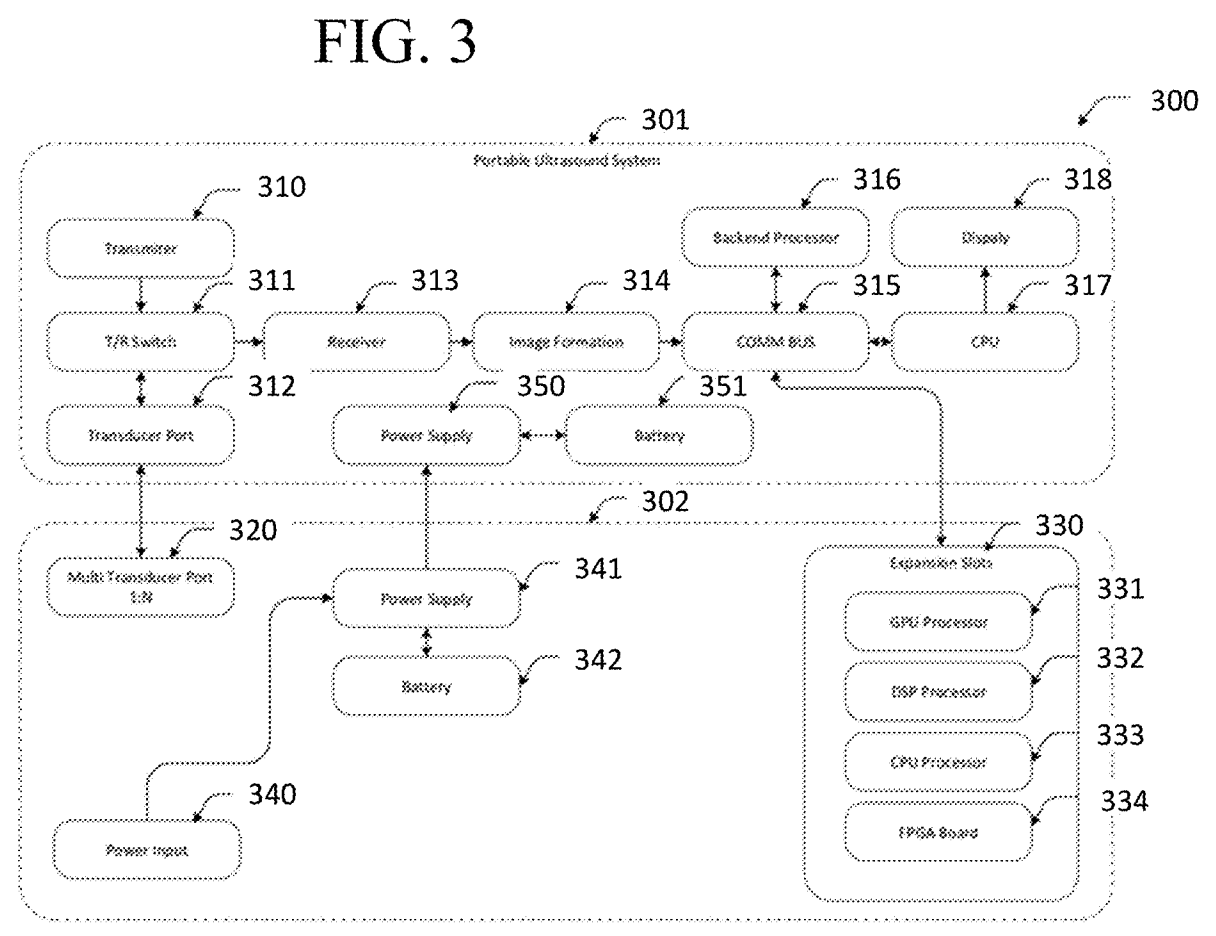

FIG. 3 shows a block diagram of a distributed ultrasound system 300 with an expansion communication bus for enhanced image processing capabilities. This block diagram consists of two primary systems, a portable ultrasound system 301 and an external ultrasound docking unit 302. The portable ultrasound system 301 can function according to an applicable portable ultrasound system for gathering channel domain data and generating one or more ultrasound images, such as the portable ultrasound system 202 shown in FIG. 2. The external ultrasound docking unit 302 functions according to an applicable ultrasound docking unit for offloading processing from a portable ultrasound system, such as the external ultrasound docking unit 204 shown in FIG. 2.

The portable ultrasound system 301 can be a fully functioning ultrasound system that can operate independently from the external ultrasound docking unit 302. This portable ultrasound system 301 can have standard as well as non-standard capabilities to enable it to augment the overall performance of the system when connected to the external ultrasound docking unit 302. Specifically, the portable ultrasound system 301 can offload image processing to the external ultrasound docking unit 302 to augment overall performance of the distributed ultrasound system 300.

The portable ultrasound system 301 includes one or more transmitters 310 for transmitting ultrasound waves into a region under investigation. The signals from the transmitters 310 can be passed through a T/R switch 311 to a transducer port 312. A transducer can be connected to the transducer port 312 where the signals can be transmitted and received from interactions with the region under investigation. Further, a transducer can be connected to a multi-transducer port 320 in the external ultrasound docking unit 302 to transmit and receive signals to and from a region under investigation. Received signals can pass through the transducer port 312 and the T/R switch 311 to the receiver 313. The receiver 313 can amplify and digitize these signals. The receiver 313 can also amplify these signals at different values based on the depth of where the signals are received. The digitized signals from the receiver 313 can then be passed to the image formation module 314 where the ultrasound image is formed.

Once image formation is completed by the image formation module 314, the data of the images can be transferred across a COMM BUS 315 to several different locations depending on the connectivity as well as what processing is required for the image data. Specifically, if the portable ultrasound system 301 is not coupled, e.g. electrically coupled, to the external ultrasound docking unit 302, then the images can be backend processed by the backend processing module 316. Specifically, the image data can be processed and formatted by the backend processing module 316 in a manner for viewing. As follows, after backend processing by the backend processing module 316, the data can be transferred over the COMM BUS 315 to the CPU 317 and subsequently displayed on the display 318 for viewing at the portable ultrasound system 301.

If the portable ultrasound system 301 is connected to the external ultrasound docking unit 302, then the image data generated by the image formation module 314 can be transferred over the COMM BUS 315 to the expansion slots 330 of the external ultrasound docking unit 302. The expansion slots 330 contain one or a combination of a GPU Processor 331, a DSP Processor 332, a CPU Processor 333, and an FPGA Board 334. These processors 331-334 can be configured to process the image data received from the COMM BUS 315.

Once the data is done being processed by the expansion slots 330, the data can be transferred back over the COMM BUS 315 to the backend processor 316. Specifically, the data can be transferred to the backend processor 316 if additional processing or data formatting is needed. Alternatively, the data, after being processed by the expansion slots 330, can be directly transferred to the CPU 317 for presentation on the display 318.

Beyond just modules for performing the previously described image processing path, the portable ultrasound system 301 can also include a power supply 350 and a battery 351. The power supply 350 can provide a regulated power supply to the portable ultrasound system 301, including the above-mentioned modules for performing image processing both at the portable ultrasound system 301 and for offloading image processing from the portable ultrasound system 301. The power supply 350 can receive power from one or a combination of the battery 351, integrated as part of the portable ultrasound system 301, a power supply 341 of the external ultrasound docking unit 302, and an external power supply, e.g. a wall main power supply. Specifically, the external ultrasound docking unit 302 includes a power supply 341 that can provide power to the portable ultrasound system 301 when docked. The power supply 341 can provide all or a portion of regulated power to the sub systems within and connected to the external ultrasound docking unit 302. For example, the expansion slots 330 and the processing boards within the expansion slots 330 can receive power from the power supply 341. The power supply 341 can also provide power to the multi-transducer port 320, e.g. to switch between active transducers. The power supply 341 can obtain power from either a battery 342, integrated as part of the external ultrasound docking unit 302, or from power input 340 that is connected to an external power supply, e.g. a main wall power supply.

Figure 4:
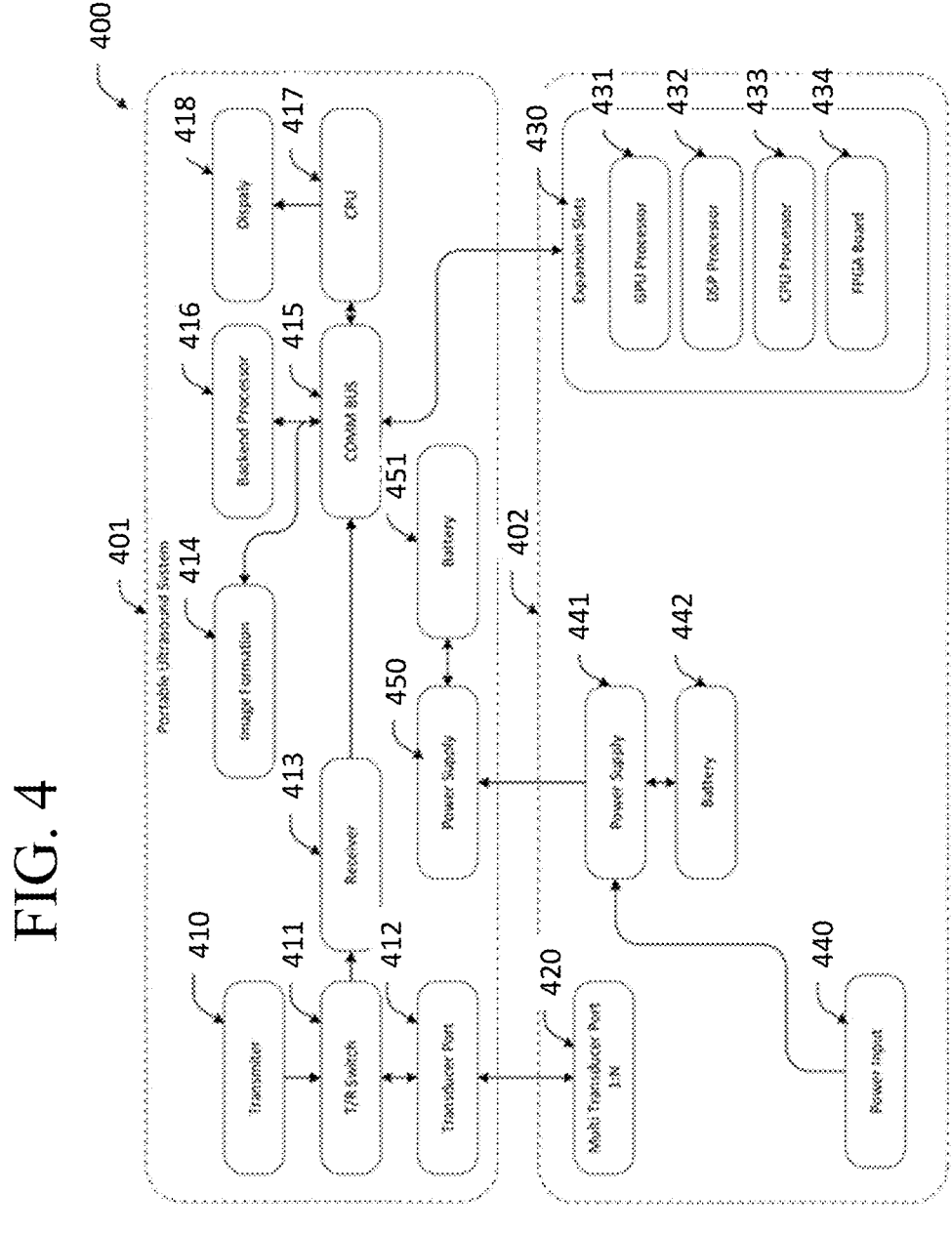
FIG. 4 shows a block diagram of another distributed ultrasound system with an expansion communication bus for enhanced image formation and image processing capabilities.

FIG. 4 shows a block diagram of another distributed ultrasound system 400 with an expansion communication bus for enhanced image formation and image processing capabilities. This block diagram consists of two primary systems, a portable ultrasound system 401 and an external ultrasound docking unit 402. The portable ultrasound system 401 can function according to an applicable portable ultrasound system for gathering channel domain data and generating one or more ultrasound images, such as the portable ultrasound system 202 shown in FIG. 2. The external ultrasound docking unit 402 functions according to an applicable ultrasound docking unit for offloading processing from a portable ultrasound system, such as the external ultrasound docking unit 204 shown in FIG. 2.

The portable ultrasound system 401 can be a fully functioning ultrasound system that can operate independently from the external ultrasound docking unit 402. This portable ultrasound system 401 can have standard as well as non-standard capabilities to enable it to augment the overall performance of the system when connected to the external ultrasound docking unit 402. Specifically, the portable ultrasound system 401 can offload image processing to the external ultrasound docking unit 402 to augment overall performance of the distributed ultrasound system 400.

The portable ultrasound system 401 can include one or more transmitters 410 for transmitting ultrasound waves into a region of interest. The signals from the transmitters 410 can be passed through a T/R switch 411 to the transducer port 412. A transducer can be connected to the transducer port 412 where the signals are transmitted and received from interactions with the region being investigated. Further, the transducer port 412 can be connected to a multi-transducer port 420. The multi-transducer port 420 can be implemented as part of the external ultrasound docking unit 402 such that the transducer would then be connected to the multi-transducer port 420 to transmit and receive signals for interaction with a region being investigated. The received signals can pass through the transducer port 412 and the T/R switch 411 to the receiver 413.

The receiver 413 can amplify and digitize the received signals. Specifically, the receiver 413 can amplify received signals at different values based on the depth of where the signals are received. The digitized signals from the receiver 413 can then be passed on to the COMM BUS 415. The COMM BUS 415 can transfer the data to the image formation module 414 when the system 400 is operating in a portable format. Once the image is formed, the data can then be passed again to the COMM BUS 415 to the backend processing 416 module. The backend processing module 416 can process and format the image data in a manner suitable for viewing. The data can then be transferred across the COMM BUS 415 to the CPU 417 and to the display 418 for viewing.

Alternatively, if the portable ultrasound system 401 is docked in the external ultrasound docking unit 402, then the image formation module 414 and the backend processing module 416 tasks can be augmented through the additional processing capabilities contained within the external ultrasound docking unit 402, e.g. through the expansion slots

430. The types of processors included in the expansion slots 430 can include one or an applicable combination of a GPU Processor 431, a DSP Processor 432, a CPU Processor 433, and an FPGA Board 434.

Beyond just modules for performing the previously described image processing path, the portable ultrasound system 401 can also include a power supply 450 and a battery 451. The power supply 450 can provide a regulated power supply to the portable ultrasound system 401, including the above-mentioned modules for performing image processing both at the portable ultrasound system 401 and for offloading image processing from the portable ultrasound system 401. The power supply 450 can receive power from one or a combination of the battery 451, integrated as part of the portable ultrasound system 401, a power supply 441 of the external ultrasound docking unit 402, and an external power supply, e.g. plugged into a wall main power supply. Specifically, the external ultrasound docking unit 402 includes a power supply 441 that can provide power to the portable ultrasound system 401 when docked. The power supply 441 can provide all regulated power to the sub systems within and connected to the external ultrasound docking unit 402. For example, the expansion slots 430 and the processing boards within the expansion slots 431-434 can receive power from the power supply 441. The power supply 441 can also provide power to the multi transducer port 420, e.g. to switch between active transducers. The power supply 441 can obtain power from either a battery 442, integrated as part of the external ultrasound docking unit 402, or from power input 440 that is connected to an external power supply, e.g. a main power supply through a wall.

Figure 5:
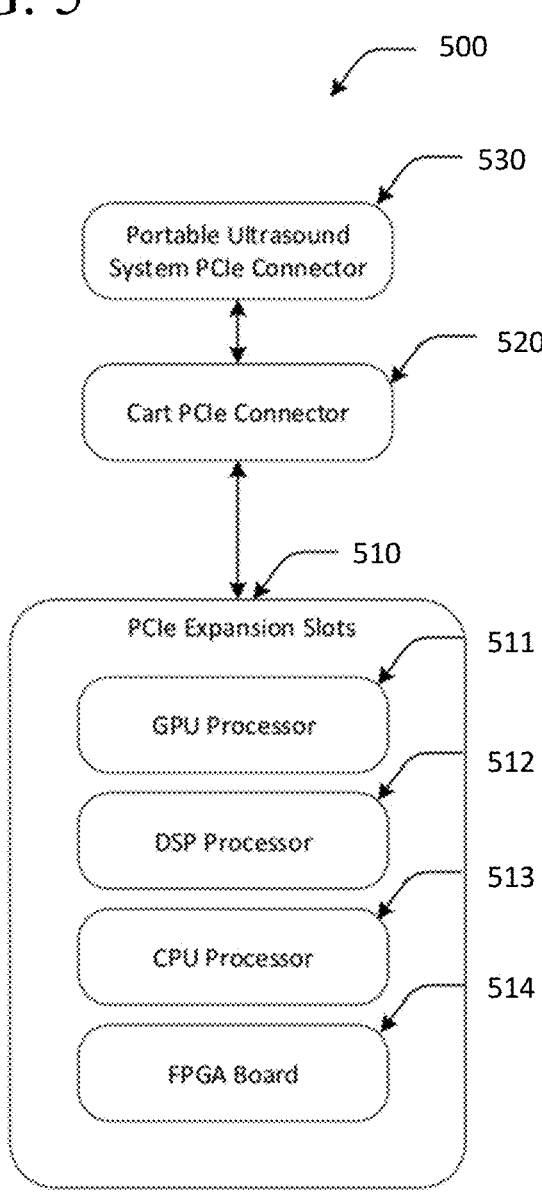
FIG. 5 shows a block diagram of a system including a signal bus between a portable ultrasound system and expansion slots of an external docking unit, e.g. an ultrasound cart.

FIG. 5 shows a block diagram of a system 500 including a signal bus between a portable ultrasound system and expansion slots of an external docking unit, e.g. an ultrasound cart. The PCIe expansion slots 510 are a possible implementation given that PCIe is a current industry standard. Further, the PCIe expansion slots 510 are a possible implementation given that PCIe has sufficient data bandwidth to transfer information.

The PCIe expansion slots 510 can contain a number of PCIe compatible cards. Specifically, the slots 510 can contain expansion cards dedicated to enhance processing capabilities but would not be limited by any specific PCIe expansion slow, as any PCIe expansion compatible card could be connected. For example, there might be a desire, e.g. of research groups, to create a PCIe card to grab data directly from the PCIe bus. Example types of cards that can be contained in the PCIe expansion slots 510 include a GPU Processor 511, a DSP processor 512, a CPU processor 513, and an FPGA board 514. GPUs are extremely efficient in handling well-structured massively parallel applications. That is advantageous as a number of applications and processes in ultrasound are well aligned. Another possible card is a DSP processor(s) 512 as DSP processors tend to be very efficient in tasks that have sections that are well structured along with some degree of decision-based logic as well. Further, CPU processor(s) 513 can be used as CPU processors tend to be very efficient on decision-based logic tasks with a lower level of efficiency in massively parallel well-structured tasks. Another type of board that can be contained in the PCIe expansion slots 510 includes an FPGA board 514. An FPGA board is good at handling massively parallel tasks in an energy efficient manner. However, FPGA boards require more time and effort to develop code for than the other processors.

The PCIe expansion slots 510 can have a physical connector 520 on the docking unit 502. Specially, the connection 520 can be configured to mate with a portable ultrasound system PCIe connector 530 when the portable ultrasound system is docked on the cart/ultrasound docking unit. The portable ultrasound system can then utilize the resources of the expansion cards contained inside the PCIe expansion slots 510 through the PCIe bus 520.

FIG. 6 is a flowchart 600 of an example method of providing a distributed ultrasound system configured to offload processing from a portable ultrasound system in the distributed ultrasound system. The example method shown in FIG. 6, can be implemented using an applicable distributed ultrasound system, such as the systems 200, 300, 400, and 500 shown in FIGS. 2-5.

At step 602, a portable ultrasound system is provided to a user. The portable ultrasound system can form part of a distributed ultrasound system. The portable ultrasound system can include a portable ultrasound processing unit configured to perform ultrasound image processing to generate ultrasound images. Further, the portable ultrasound system can include a transmitter(s) and a receiver(s) for transmitting and receiving ultrasound waves into and from a subject area in order to generate channel domain data. Subsequently, the portable ultrasound processing unit can apply ultrasound image processing to the channel domain data to generate the ultrasound images.

At step 604, an external ultrasound docking unit is provided to the user. The external ultrasound docking unit can form the distributed ultrasound system with the portable ultrasound system. The external ultrasound docking unit can be configured to offload at least a portion of the ultrasound image processing from the portable ultrasound system in order to generate the ultrasound images. Specifically, the external ultrasound docking unit can offload the ultrasound image processing from the portable ultrasound system when the portable ultrasound system is electrically coupled, and potentially physically secured, to the external ultrasound docking unit. The external ultrasound docking unit can be implemented as part of an ultrasound cart.

FIG. 7 is a flowchart 700 of an example method of offloading processing from a portable ultrasound system in a distributed ultrasound system. The example method shown in FIG. 7, can be implemented using an applicable distributed ultrasound system, such as the systems 200, 300, 400, and 500 shown in FIGS. 2-5.

At step 702, a portable ultrasound system is coupled to an external ultrasound docking unit. The portable ultrasound system can be electrically coupled to the external ultrasound docking unit, and potentially physically coupled to the external ultrasound docking unit. For example, the portable ultrasound system can be coupled to the external ultrasound docking unit through a communication bus. The portable ultrasound system can be configured to perform ultrasound image processing for generating ultrasound images. Specifically, the portable ultrasound system can be configured to perform ultrasound image processing on channel domain data gathered by the portable ultrasound system in order to generate ultrasound images.

At step 704, at least a portion of the ultrasound image processing is offloaded from the portable ultrasound system to the external ultrasound docking unit to generate the ultrasound images. Specifically, the ultrasound image processing can be offloaded to the external ultrasound docking unit through an electrical coupling between the portable ultrasound system and the external ultrasound docking unit. For example, channel domain data can be transferred from the portable ultrasound system to the external ultrasound docking unit as part of offloading processing to the external ultrasound docking unit. In another example, beamformed data can be transferred from the portable ultrasound system to the external ultrasound docking unit as part of offloading processing to the external ultrasound docking unit. In yet another example, ultrasound images can be transferred from the portable ultrasound system to the external ultrasound docking unit, where backend processing can further be applied to the ultrasound images.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A distributed ultrasound system comprising:
   a portable ultrasound system comprising:
      one or more transmitters configured to transmit ultrasound waves into a subject region;

one or more receivers configured to receive ultrasound waves from the subject region in response to the ultrasound waves transmitted into the subject region; and a portable ultrasound processing unit configured to perform ultrasound image processing for generating one or more ultrasound images of the subject region using, at least in part, the ultrasound waves received from the subject region by the one or more receivers, wherein the portable ultrasound system is handheld and capable of being moved over a patient's body to an area proximate to the subject region; and an external ultrasound docking unit configured to receive and electrically couple with the portable ultrasound system and offload at least a portion of the ultrasound image processing from the portable ultrasound system when the portable ultrasound system is coupled to the external ultrasound docking unit, wherein the portable ultrasound system determines whether to offload the at least a portion of the ultrasound image processing in response to determination by a machine-learning system that, during an examination, an ultrasound operation cannot be completed in real-time by the portable ultrasound processing unit.

2. The distributed ultrasound system of claim 1, further comprising:

a temperature sensor, wherein the portable ultrasound system determines whether to offload the at least a portion of the ultrasound image processing based on input from the temperature sensor.

3. The distributed ultrasound system of claim 1, further comprising:

a battery-level sensor, wherein the portable ultrasound system determines whether to offload the at least a portion of the ultrasound image processing based on input from the battery-level sensor.

4. The distributed ultrasound system of claim 1, wherein the portable ultrasound system is configured to beamform channel domain data obtained from the ultrasound waves to generate beamformed data processed by the external ultrasound docking unit to generate ultrasound images, and wherein the portable ultrasound processing unit is configured to continue to generate additional beamformed data while the external ultrasound docking unit processes the beamformed data already generated by the portable ultrasound processing unit.

5. The distributed ultrasound system of claim 1, wherein the external ultrasound docking unit is further configured to provide power to the portable ultrasound system when the portable ultrasound system is coupled to the external ultrasound docking unit.

6. The distributed ultrasound system of claim 1, wherein the portable ultrasound system further comprises a power supply and the external ultrasound docking unit is further configured to charge the power supply of the portable ultrasound system when the portable ultrasound system is coupled to the external ultrasound docking unit.

7. The distributed ultrasound system of claim 1, wherein the external ultrasound docking unit is integrated as part of a portable ultrasound cart.

8. The distributed ultrasound system of claim 1, wherein the portable ultrasound system is automatically electrically coupled to the external ultrasound docking unit when the portable ultrasound system is physically connected to the external ultrasound docking unit.

9. The distributed ultrasound system of claim 1, wherein the portable ultrasound system is manually electrically coupled to the external ultrasound docking unit when the portable ultrasound system is physically connected to the external ultrasound docking unit.

10. The distributed ultrasound system of claim 1, wherein the portable ultrasound system is electrically coupled to the external ultrasound docking unit in a removable manner through a communication bus.

11. The distributed ultrasound system of claim 10, wherein the communication bus is configured to provide power and either or both data input and data output to the portable ultrasound system from the external ultrasound docking unit.

12. The distributed ultrasound system of claim 10, wherein the communication bus is an industry standard bus.

13. The distributed ultrasound system of claim 1, wherein the portable ultrasound processing unit is further configured to:

determine whether to offload the at least the portion of the ultrasound image processing to the external ultrasound docking unit based on whether the portable ultrasound system is coupled to the external ultrasound docking unit; and offload the at least the portion of the ultrasound image processing to the external ultrasound docking unit if it is determined to offload the at least the portion of the ultrasound image processing to the external ultrasound docking unit.

14. The distributed ultrasound system of claim 13, wherein the portable ultrasound processing unit is further configured to:

generate, at the portable ultrasound system, the one or more ultrasound images of the subject region; and perform backend processing of the one or more ultrasound images at the portable ultrasound system, as part of performing the at least the portion of the ultrasound image processing at the portable ultrasound system, if it is determined to refrain from offloading the at least the portion of the ultrasound image processing to the external ultrasound docking unit.

15. The distributed ultrasound system of claim 13, wherein the portable ultrasound processing unit is further configured to determine whether to offload the at least the portion of the ultrasound image processing based on processing characteristics of the at least the portion of the ultrasound image processing.

16. The distributed ultrasound system of claim 13, wherein the portable ultrasound processing unit is further configured to:

generate, at the portable ultrasound system, the one or more ultrasound images of the subject region; and send the one or more ultrasound images to the external ultrasound docking unit as part of offloading the at least the portion of the ultrasound image processing to the external ultrasound docking unit if it is determined to offload the at least the portion of the ultrasound image processing to the external ultrasound docking unit.

17. The distributed ultrasound system of claim 16, wherein the external ultrasound docking unit is further configured to perform enhanced backend processing of the one or more ultrasound images as part of performing the at least the portion of the ultrasound image processing offloaded to the external ultrasound docking unit.

18. The distributed ultrasound system of claim 13, wherein:

the portable ultrasound processing unit is further configured to send received data of the received ultrasound waves from the subject region if it is determined to offload the at least the portion of the ultrasound image processing to the external ultrasound docking unit; and the external ultrasound docking unit is further configured to generate the one or more ultrasound images of the subject region using the received data of the received ultrasound waves from the subject region.

19. The distributed ultrasound system of claim 18, wherein the external ultrasound docking unit is further configured to:

perform enhanced backend processing on the one or more ultrasound images generated at the ultrasound docking unit to generate one or more enhanced backend processed ultrasound images as part of offloading the at least the portion of the ultrasound image processing to the external ultrasound docking unit; and send the one or more enhanced backend processed ultrasound images to the portable ultrasound processing unit for display of the one or more ultrasound images of the subject region.

* * * * *